United States Patent [19]

Waranis et al.

[11] Patent Number: 5,516,770

[45] Date of Patent: May 14, 1996

[54] RAPAMYCIN FORMULATION FOR IV INJECTION

[75] Inventors: Robert P. Waranis, Chazy, N.Y.; Thomas W. Leonard, Wilmington, N.C.

[73] Assignee: American Home Products Corporation, Madison, N.J.

[21] Appl. No.: 308,923

[22] Filed: Sep. 22, 1994

Related U.S. Application Data

[63] Continuation-in-part of Ser. No. 129,525, Sep. 30, 1993, abandoned.

[51] Int. Cl.$^6$ .................................................. A61K 31/33
[52] U.S. Cl. ............................................................ 514/183
[58] Field of Search ............................................... 514/183

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,885,171 | 12/1989 | Surendra et al. | 424/122 |
| 5,080,899 | 1/1992 | Sturm et al. | 514/291 |
| 5,100,899 | 3/1992 | Calne | 514/291 |

FOREIGN PATENT DOCUMENTS

| | | |
|---|---|---|
| 0041795 | 12/1981 | European Pat. Off. . |
| 042816 | 5/1991 | European Pat. Off. . |
| 0444659 | 9/1991 | European Pat. Off. . |

OTHER PUBLICATIONS

Physicians'Desk Reference, 45th ed., 1991, pp. 2119–2122, Medical Economics Company, Inc.
Physicians'Desk Reference, 45th ed., 1991, pp. 785–787, Medical Economics Company, Inc.
Luke et al., Effects of Cyclosporine on the Isolated Perfused Rat Kidney, Transplantation, vol. 43, No. 6, pp. 795–799, 1987.
Venkataram, et al., Pharmacokinetics of Two Alternative Dosage Forms for Cyclosporine: Liposomes and Intralipid, Journal of Pharmaceutical Sciences, vol. 79, No. 3, pp. 216–219 1990.
Thiel, et al., Acutely Impaired Renal Function During Intravenous Administration of Cyclosporine A; A Cremaphore Side–Effect, Clinical Nephrology, vol. 25, Suppl. No. 1., pp. S40–42, 1986.
Honbo, et al., The Oral Dosage Form of FK–506, Transplantation Proceedings, vol. XIX, No. 5, Suppl. 6, pp. 17–22, 1987.
Stepkowski, et al., Rapamycin, A Potent Immunosuppressive Drug for Vascularized Heart, Kidney, and Small Bowel Transplantation in the Rat, Transplantation, vol. 51, No. 1, pp. 22–24, 1991.
Kahan, et al., Synergistic Interactions of Cyclosporine and Rapamycin to Inhibit Immune Performances of Normal Human Peripheral Blood Lymphocytes In Vitro, Transplantation, vol. 51, No. 1, pp. 232–237, 1991.
Intl. Pharm. Abstracts—FK–506, Immunosuppressant for the 1990s, Macleod, et al., Lancet, 337, pp. 25–27, Jan. 5, 1991.
Intl. Pharm. Abstracts, FK–506: Discussion of a New Investigationsl Drug, C. G. Forde, ASHP Midyear Clinical Meeting, 25, p. 446D, Dec. 1990.
Intl. Pharm. Abstracts, FK–506, Kidney Transplantation Under FK 506, Starzl, et al., JAMA, 264, pp. 63–67, Jul. 4, 1990.
Intl. Pharm. Abstracts—FK–506 In Steroid–Resistant Focal Sclerosing Glomerulonephritis of Childhood, McCauley, et al., Lancet, 335, p. 674, Mar. 17, 1990.
Intl. Pharm. Abstracts, New Drug Could Replace Cyclosporin in Transplant Drug Therapy, Anon, Am. Pharm. NS, 30, 16, Jan. 1990.
Intl. Pharm. Abstracts, Treatment of Cyclosporin Induced Hemolytic–Uremic Syndrome with FK–506, McCauley, et al., Lancet, 2, 1516, Dec. 23–30, 1989.
Intl. Pharm. Abstracts—FK–506 for Liver, Kidney, and Pancreas Transplantation; Starzl, et al., Lancet, 2, 1000–1004, Oct. 28, 1989.

*Primary Examiner*—Marianne M. Cintins
*Assistant Examiner*—Phyllis G. Spivack
*Attorney, Agent, or Firm*—Arthur G. Seifert

[57] ABSTRACT

Disclosed herein is an aqueous, injectable rapamycin solution, obtained by a process consisting of mixing 5 to 30 volume percent of a concentrate solution of rapamycin in propylene glycol, at concentrations of rapamycin ranging from 0.5 mg/ml to 10 mg/ml, with a diluent solution consisting of 0.1 to 10 weight percent of one or more polyoxyethylene sorbitan esters, 10 to 60 weight percent of polyethylene glycol 200, 300 or 400 or a combination thereof and 30 to 89.9 volume percent water, wherein the concentration of rapamycin in the injectable solution ranges from 0.025 mg/ml to 3 mg/ml.

28 Claims, No Drawings

RAPAMYCIN FORMULATION FOR IV INJECTION

This application is a continuation-in-part of U.S. patent application Ser. No. 08/129,525, filed on Sep. 30, 1993, now abandoned.

The invention disclosed herein provides an aqueous formulation of rapamycin for intravenous injection (iv). In one aspect the invention comprises a concentrate solution of rapamycin in propylene glycol, in combination with a diluent consisting of a polyoxyethylene sorbitan ester, polyethylene glycol 400 and water, all in given proportions as described below.

BACKGROUND OF THE INVENTION

Rapamycin is a macrolide antibiotic produced by *Streptomyces hygroscopicus* which was discovered first for its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigation has begun for the use of rapamycin in inhibiting rejection in transplantation in man.

Rapamycin is insoluble in water and is only slightly soluble in solubilizers, such as propylene glycol, glycerin and PEG 400, commonly used in preparing parenteral formulations. It is only sparingly soluble in PEG 300 and is insoluble or very slightly soluble in commonly used aqueous injectable co-solvent systems, such as, 20% ethanol/water, 10% DMA/water, 20% Cremophor® EL/water and 20% polysorbate 80/water. For these reasons clinically and commercially acceptable injectable formulations of rapamycin have been difficult to make. An injectable composition of rapamycin is described in European Patent Publication No. 0041795, published Dec. 16, 1981. In this injectable formulation rapamycin is first dissolved in a low boiling point organic solvent, namely, acetone, methanol or ethanol. This solution is then mixed with a nonionic surfactant selected from polyoxyethylated fatty acids; polyoxyethylated fatty alcohols; and polyoxyethylated glycerin hydroxy fatty acid esters, e.g. polyoxyethylated castor oil, exemplified by Cremophor® EL and polyoxyethylated hydrogenated castor oil, exemplified by Cremophor® RH 40 and Cremophor® RH 60. Cremophor® EL is the primary nonionic surfactant used in the examples.

The primary immunosuppressive agent presently used for inhibiting rejection in the allograft transplantation of organs in man is cyclosporine (Sandimmune®). Cyclosporine is a cyclic polypeptide consisting of 11 amino acids. The intravenous injectable formulation of Sandimmune® (IV) is a sterile ampul containing, per ml, 50 mg of cyclosporine, 650 mg of Cremophor® EL and alcohol Ph Helv. (32.9% by volume) (under nitrogen). For administration this mixture is diluted further with 0.9% Sodium Chloride Injection or 5% Dextrose Injection before use. (*Physicians' Desk Reference*, 45th ed., 1991, pp. 1962–64, Medical Economics Company, Inc.) The macrolide molecule designated FK506, which has certain structural similarities to rapamycin, is also currently undergoing clinical investigation for inhibiting rejection in allograft organ transplantation in man. FK506 is isolated from *Streptomyces tsuskubaensis* and is described in U.S. Pat. No. 4,894,366 to Okuhara et al., issued Jan. 16, 1990 R. Venkataramanan et al., in Transplantation Proceedings, 22, No. 1, Suppl., 1 pp 52–56 (February 1990), report that the intravenous injectable formulation of FK506 is provided as a 10 mg/ml solution of FK506 in polyoxyethylated castor oil (HCO-60, a surfactant) and alcohol. The intravenous preparation must be diluted with saline or dextrose and administered as an infusion for 1 to 2 hours.

DETAILED DESCRIPTION OF THE INVENTION

One aspect of this invention is an aqueous-based, injectable rapamycin solution comprising a concentrate solution of rapamycin in propylene glycol in combination with a diluent solution comprising a polyoxyethylene sorbitan ester, polyethylene glycol 200, 300 or 400 or a combination thereof and water. Specifically, in a first aspect, Applicants' invention provides an aqueous, injectable rapamycin solution obtainable by mixing 5 to 30 volume percent of a concentrate solution of rapamycin in propylene glycol, at concentrations of rapamycin ranging from 0.5 mg/ml to 10 mg/ml, with a diluent solution comprising 0.1 to 10 weight percent of one or more polyoxyethylene sorbitan esters, 10 to 60 weight percent of polyethylene glycol 200, 300 or 400 or a combination thereof and 30 to 89.9 volume percent water, wherein the concentration of rapamycin in the combined solution ranges from 0.025 mg/ml to 3 mg/ml. Preferred aqueous, injectable rapamycin solutions are those wherein one polyoxyethylene sorbitan ester is present and the polyethylene glycol present is polyethylene glycol 400.

Preferred aqueous, injectable rapamycin solutions of this aspect of the invention are those in which the concentration of rapamycin in the propylene glycol concentrate ranges from 2 mg/ml to 8 mg/ml. More preferred are those in which the concentration of rapamycin in the propylene glycol concentrate ranges from 4 mg/ml to 6 mg/ml. Also preferred aqueous, injectable rapamycin solutions of the invention are those in which the concentration of rapamycin in the combined solution ranges from 0.2 mg/ml to 4 mg/ml and those wherein the propylene glycol concentrate of rapamycin comprises 10 to 25 weight percent of the total solution.

Further preferred aqueous, injectable rapamycin solutions of the invention are those in which the diluent comprises 1.0 to 8 weight percent polyoxyethylene sorbitan ester, 10 to 50 percent polyethylene glycol 400, and 42 to 89 volume percent of water. Also preferred are aqueous, injectable rapamycin solutions of the invention in which 31 to 80 percent by volume of the total solution is water.

Further preferred aqueous, injectable rapamycin solutions of the invention are those obtainable by a process comprising mixing 10 to 25 volume percent of a concentrate solution of rapamycin in propylene glycol, at concentrations of rapamycin ranging from 2 mg/ml to 8 mg/ml, with a diluent solution comprising 1 to 8 weight percent of a polyoxyethylene sorbitan ester, 10 to 50 weight percent polyethylene glycol 300 or 400 or a combination thereof, and 42–89 volume percent water, wherein the concentration of rapamycin in the injectable solution ranges from 0.2 mg/ml to 2 mg/ml.

Especially preferred aqueous, injectable rapamycin solutions according to this aspect of the invention comprise 10 to 20 volume percent of a concentrate solution of rapamycin in propylene glycol, at concentrations of rapamycin ranging from 4 mg/ml to 6 mg/ml, in combination with a diluent solution comprising 2 to 7.5 weight percent of a polyoxyethylene sorbitan ester, 10 to 50 weight percent polyethylene glycol 400 and 42.5 to 88 volume percent water, wherein the concentration of rapamycin in the combined solution ranges from 0.4 mg/ml to 1.2 mg/ml. The diluent of example 3A and the combined injectable solution of example 3B are particularly preferred.

In a second aspect, this invention provides a pharmaceutical product containing a concentrate solution of rapamycin and a diluent, as a combined preparation for mixing prior to IV injection to give a solution having a concentration of rapamycin in the range 0.025 mg/ml to 3 mg/ml; said concentrate solution comprising rapamycin in propylene glycol in the range 0.5 mg/ml to 10 mg/ml; and said diluent solution comprising 0.1 to 10 weight percent of one or more polyoxyethylene sorbitan esters, 10 to 60 weight percent of either polyethylene glycol 200, 300 or 400 or a combination thereof and 30 to 89.9 volume percent water. Preferred and especially preferred embodiments of this aspect of the invention have the same composition of the concentrate and diluent and rapamycin in the concentrate and in the injectable solution as those described above for the first aspect of the invention.

In a third aspect of this invention provides an aqueous, injectable solution of rapamycin, said solution comprising rapamycin in 5 to 30 weight percent propylene glycol, 0.07 to 9.5 weight percent of one or more polyoxyethylene sorbitan esters, 7 to 57 weight percent of polyethylene glycol 200, 300 or 400 or a combination thereof and 21 to 85.4 volume percent of water, wherein the concentration of rapamycin in the solution ranges from 0.025 mg/ml to 3 mg/ml.

Preferred aqueous, injectable rapamycin solutions of this aspect of the invention are those wherein the concentration of rapamycin in the solution ranges from 0.2 mg/ml to 2 mg/ml. Also preferred, independently, are those wherein the propylene glycol comprises 10 to 25 volume percent of the solution, the polyoxyethylene sorbitan ester comprises 0.75 to 7.2 percent by weight, the polyethylene glycol 400 comprises 7.5 to 45 weight percent of the solution, and water comprises 31 to 80 percent by volume of the total solution.

Especially preferred aqueous, injectable solutions of rapamycin, of this aspect of the invention comprise rapamycin in 10 to 25 volume percent propylene glycol, 0.75 to 7.2 weight percent of a polyoxyethylene sorbitan ester, 7.5 to 45 weight percent polyethylene glycol 400 and 31 to 80 volume percent of water, wherein the concentration of rapamycin in the solution ranges from 0.2 mg/ml to 2.0 mg/ml.

The aqueous, injectable rapamycin solutions of the invention are preferred for administration by bolus injection, rather than by infusion, particularly for such solutions where the concentration of rapamycin in the combined solution is greater than 0.1 mg/ml. Where infusion is appropriate, an infusion period of less than 24 hours is preferred. An infusion period of one-quarter hour to 6 hours is particularly preferred.

The manufacture of rapamycin iv concentrate comprises adding the rapamycin to the propylene glycol and mixing until a solution results, which may be accomplished at room temperatures. The solution is then filtered in a known manner for sterility. Appropriate volumes of the concentrate solution are filled into ampules which are then sealed in a known manner. In accordance with standard manufacturing procedures for injectables, sterile conditions are maintained throughout the filtering, filling and sealing operations. The product rapamycin concentrate is best stored under refrigeration.

The manufacture of each of the rapamycin iv diluent systems comprises weighing the polysorbate 80 into a suitable container, adding the appropriate amounts of PEG 200, 300 and/or 400 and water for injection and mixing until a solution results. Appropriate volumes of diluent are filled into vials which are then stoppered, sealed and autoclaved. The completed rapamycin diluent solution may be stored at room temperature or under refrigeration.

The procedure for constituting the final formulas for administration comprises injecting an aliquot of rapamycin iv concentrate into a vial containing the rapamycin iv diluent, shaking for approximately one minute or until a clear solution results. The constituted solution should be administered within the stated use period. The use period of constituted rapamycin injectable solutions is the period of time during which the constituted solution remains clear and colorless. The use period may range up to 4 hours, but a use period of 1 hour is preferred.

Accordingly this invention also provides a process for preparing an aqueous, injectable rapamycin solution which comprises mixing 5 to 30 volume percent of a concentrate solution of rapamycin in propylene glycol, at concentrations of rapamycin ranging from 0.5 mg/ml to 10 mg/ml, with a diluent solution comprising 0.1 to 10 weight percent of one or more polyoxyethylene sorbitan esters, 10 to 60 weight percent of polyethylene glycol 200, 300 or 400 or a combination thereof and 30 to 89.9 volume percent water, wherein the concentration of rapamycin in the injectable solution ranges from 0.025 mg/ml to 3 mg/ml. It will be appreciated by those skilled in the art that the object of the invention may be accomplished in other ways, for example by mixing some of the propylene glycol in the diluent solution and/or, conversely, by mixing some or all of the PEG in the concentrate solution.

Preferred polyoxyethylene sorbitan esters are polysorbate 20, 60 or 80, of which polysorbate 80 is particularly preferred. Propylene glycol, Polysorbate 80 and PEG 200, 300 and 400 are readily available commercial products for use in pharmaceutical manufacturing. PEG 300 and 400 may be obtained from J. T. Baker Inc. of Phillipsburg, N.J., and polysorbate 80 may be obtained from ICI America, Inc. of Wilmington, Del.

The following examples further illustrate the practice of the invention.

EXAMPLE 1

Preparation of Rapamycin IV Concentrate in Propylene Glycol (6 mg/ml)

Rapamycin IV Concentrate in Propylene Glycol (6 mg/ml)

Formula (Density—1.036 g/ml)

| Ingredients | Amount |
| --- | --- |
| Rapamycin @ 100% | 0.6 gm |
| Propylene Glycol, USP qs | 100 ml or 103.6 gm |

Procedure

1. Weigh the rapamycin into a suitably calibrated container.
2. Adjust volume to 100 ml with Propylene Glycol.
3. Mix until a uniform solution results.
4. Sterile filter the solution.
5. Package into ampules and seal.

EXAMPLE 2

Preparation of Rapamycin IV solution at 1.0 mg/ml

A. Diluent for Rapamycin IV at 1.0 mg/ml
Formula (Density—1.043 gm/ml)

| Ingredients | Amount |
| --- | --- |
| Polysorbate 80, NF | 1.2 gm |
| Polyethylene Glycol 400, NF | 27.1 gm |
| Water for Injection, USP qs | 100 ml or 104.3 gm |

Procedure

1. Weigh the Polysorbate 80 into a suitably calibrated container.
2. Add the Polyethylene Glycol 400 to the container in Step #1.
3. Adjust to final volume with Water for Injection, USP.
4. Mix until uniform.
5. Filter the resulting solution.
6. Fill 2.50 ml ±0.1 ml into each 5 ml flint vial, seal and crimp.
7. Autoclave to achieve sterility.

B. Rapamycin IV solution at 1.0 mg/ml (constituted)
Formula (Density—1.050 gm/ml)

| Ingredients | Amount |
| --- | --- |
| Rapamycin IV Concentrate @ 6 mg/ml | 0.5 ml |
| Diluent for IV-rapamycin | 2.5 ml |

Procedure

1. Inject 0.5 ml of Rapamycin IV Concentrate at 6 mg/ml into a vial containing 2.5 ml of diluent for IV-rapamycin using good sterile technique.
2. Shake until a clear solution results.

EXAMPLE 3

Preparation of Rapamycin IV solution at 1.0 mg/ml

A. Diluent for Rapamycin IV at 1.0 mg/ml
Formula (Density—1.043 gm/ml)

| Ingredients | Amount |
| --- | --- |
| Polysorbate 80, NF | 2.4 gm |
| Polyethylene Glycol 400, NF | 27.1 gm |
| Water for Injection, USP qs | 100 ml or 104.3 gm |

Procedure

1. Weigh the Polysorbate 80 into a suitably calibrated container.
2. Add the Polyethylene Glycol 400 to the container in Step #1.
3. Adjust to final volume with Water for Injection, USP.
4. Mix until uniform.
5. Filter the resulting solution.
6. Fill 2.50 ml ±0.1 ml into each 5 ml flint vial, seal and crimp.
7. Autoclave to achieve sterility.

B. Rapamycin IV solution at 1.0 mg/ml (constituted)
Formula (Density—1.050 gm/ml)

| Ingredients | Amount |
| --- | --- |
| Rapamycin IV Concentrate @ 6 mg/ml | 0.5 ml |
| Diluent for IV-rapamycin (from Ex. 3A) | 2.5 ml |

Procedure

1. Inject 0.5 ml of Rapamycin IV Concentrate at 6 mg/ml into a vial containing 2.5 ml of diluent for IV-rapamycin using good sterile technique.
2. Shake until a clear solution results.

What we claim is;

1. An aqueous, injectable rapamycin solution obtained by a process consisting essentially of mixing 5 to 30 volume percent of a concentrate solution of rapamycin in propylene glycol, at concentrations of rapamycin ranging from 0.5 mg/ml to 10 mg/ml, with a diluent solution consisting essentially of 0.1 to 10 weight percent of one or more polyoxyethylene sorbitan esters, 10 to 60 weight percent of polyethylene glycol 200, 300 or 400 or a combination thereof and 30 to 89.9 volume percent water, wherein the concentration of rapamycin in the injectable solution ranges from 0.025 mg/ml to 3 mg/ml.

2. An aqueous, injectable rapamycin solution according to claim 1 wherein one polyoxyethylene sorbitan ester is present.

3. An aqueous, injectable rapamycin solution according to claim 1 wherein the polyethylene glycol is polyethylene glycol 400.

4. An aqueous, injectable rapamycin solution according to claim 1 wherein the concentration of rapamycin in the propylene glycol concentrate ranges from 2 mg/ml to 8 mg/ml.

5. An aqueous, injectable rapamycin solution according to claim 1 wherein the concentration of rapamycin in the propylene glycol concentrate ranges from 4 mg/ml to 6 mg/ml.

6. An aqueous, injectable rapamycin solution according to claim 1, wherein the concentration of rapamycin in the injectable solution ranges from 0.2 mg/ml to 2 mg/ml.

7. An aqueous, injectable rapamycin solution according to claim 1 wherein the propylene glycol concentrate of rapamycin comprises 10 to 25 volume percent of the injectable solution.

8. An aqueous, injectable rapamycin solution according to claim 1 wherein the diluent consists essentially of 1.0 to 8 weight percent polyoxyethylene sorbitan ester, 10 to 50 weight percent polyethylene glycol 400, and 42 to 89 volume percent of water.

9. An aqueous, injectable rapamycin solution according to claim 1 wherein 31 to 80 percent by volume of the injectable solution is water.

10. A pharmaceutical product consisting essentially of a concentrate solution of rapamycin and a diluent, as a combined preparation for mixing prior to IV injection to give a solution having a concentration of rapamycin in the range 0.025 mg/ml to 3 mg/ml; said concentrate solution consisting essentially of rapamycin in propylene glycol in the range 0.5 mg/ml to 10 mg/ml; and said diluent solution consisting essentially of 0.1–10 weight percent of one or more polyoxyethylene sorbitan esters, 10 to 60 weight percent of either polyethylene glycol 200, 300 or 400 or a combination thereof and 30 to 89.9 volume percent water, wherein said concentrate solution comprises 5 to 30 volume percent of an injectable solution.

11. A pharmaceutical product according to claim 10 wherein one polyoxyethylene sorbitan ester is present.

12. A pharmaceutical product according to claim 10 wherein the polyethylene glycol is polyethylene glycol 400.

13. A pharmaceutical product according to claim 10 wherein the concentration of rapamycin in the propylene glycol concentrate ranges from 2 mg/ml to 8 mg/ml.

14. A pharmaceutical product according to claim 10 wherein the concentration of rapamycin in the propylene glycol concentrate ranges from 4 mg/ml to 6 mg/ml.

15. A pharmaceutical product according to claim 10, wherein the concentration of rapamycin in the solution ranges from 0.2 mg/ml to 2 mg/ml.

16. A pharmaceutical product according to claim 10 wherein the propylene glycol concentrate of rapamycin comprises 10 to 25 volume percent of the injectable solution.

17. A pharmaceutical product according to claim 10 wherein the diluent consists essentially of 1.0 to 8 weight percent polyoxyethylene sorbitan ester, 10 to 50 weight percent polyethylene glycol 400, and 42 to 89 volume percent of water.

18. An aqueous, injectable rapamycin solution, said injectable solution consisting essentially of rapamycin in 5 to 30 volume percent propylene glycol, 0.07 to 9.5 weight percent of one or more polyoxyethylene sorbitan esters, 7 to 57 weight percent of either polyethylene glycol 200, 300 or 400 or a combination thereof, and 21 to 85.4 volume percent of water, wherein the concentration of rapamycin in the injectable solution ranges from 0.025 mg/ml to 3 mg/ml.

19. An aqueous, injectable rapamycin solution according to claim 18 wherein the polyethylene glycol is polyethylene glycol 400.

20. An aqueous, injectable rapamycin solution according to claim 18 wherein one polyoxyethylene sorbitan ester is present.

21. An aqueous, injectable rapamycin solution according to claim 18, wherein the concentration of rapamycin in the injectable solution ranges from 0.2 mg/ml to 2 mg/ml.

22. An aqueous, injectable rapamycin solution according to claim 18 wherein the propylene glycol comprises 10–25 volume percent of the injectable solution.

23. An aqueous, injectable rapamycin solution according to claim 18 wherein the polyoxyethylene sorbitan ester comprises 0.75 to 7.2 weight percent of the injectable solution.

24. An aqueous, injectable rapamycin solution according to claim 18 wherein the polyethylene glycol 400 comprises 7.5 to 45 weight percent of the injectable solution.

25. An aqueous, injectable rapamycin solution according to claim 18 wherein water comprises 31 to 80 percent by volume of the total solution.

26. An aqueous, injectable rapamycin solution according to claim 18 comprising 10–25 volume percent propylene glycol, 0.75 to 7.2 weight percent of a polyoxyethylene sorbitan ester, 7.5 to 45 weight percent polyethylene glycol 400 and 31 to 80 volume percent of water, wherein the concentration of rapamycin in the injectable solution ranges from 0.2 mg/ml to 2 mg/ml.

27. An aqueous, injectable rapamycin solution, said injectable solution consisting essentially of rapamycin in 10 to 25 volume percent propylene glycol, 0.75 to 7.2 weight percent of one or more polyoxyethylene sorbitan esters, 7.5 to 45 weight percent polyethylene glycol 400, and 31 to 80 volume percent of water, wherein the concentration of rapamycin in the injectable solution ranges from 0.2 mg/ml to 2 mg/ml.

28. A pharmaceutical product consisting essentially of a concentrate solution of rapamycin and a diluent, as a combined preparation for mixing prior to IV injection to give a solution having a concentration of rapamycin in the range 0.2 mg/ml to 2 mg/ml; said concentrate solution consisting, essentially of rapamycin in propylene glycol in The range 2 mg/ml to 8 mg/ml; and said diluent solution consisting essentially of 1 to 8 weight percent polyoxyethylene sorbitan ester, 10 to 50 weight percent polyethylene glycol 400 and 42 to 89 volume percent water, wherein said concentrate solution comprises 5 to 30 volume percent of an injectable solution.

* * * * *